United States Patent
Sederstrom et al.

(10) Patent No.: US 9,352,112 B2
(45) Date of Patent: May 31, 2016

(54) SHAPED EVACUATION PORT FOR A MULTI-LUMEN TRACHEAL TUBE

(75) Inventors: Donn Sederstrom, West Linn, OR (US); Tyler Grubb, Portland, OR (US); Alexa Jansey, Culver, IN (US); Christopher Brune, Evergreen, CO (US); Corinne Lengsfeld, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 636 days.

(21) Appl. No.: 13/324,141

(22) Filed: Dec. 13, 2011

(65) Prior Publication Data

US 2013/0146063 A1    Jun. 13, 2013

(51) Int. Cl.
*A61M 16/00* (2006.01)
*A61M 16/04* (2006.01)

(52) U.S. Cl.
CPC ........... *A61M 16/04* (2013.01); *A61M 16/0431* (2014.02); *A61M 16/0479* (2014.02); *A61M 16/0486* (2014.02); *A61M 16/0434* (2013.01)

(58) Field of Classification Search
CPC ............... A61M 16/0434; A61M 16/0463; A61M 16/0475; A61M 16/0477; A61M 16/0479; A61M 16/047; A61M 16/0402; A61M 16/484; A61M 16/481; A61M 16/477; A61M 16/475
USPC .............................. 128/200.26, 207.14–207.17
See application file for complete search history.

(56) References Cited

U.S. PATENT DOCUMENTS

| | | |
|---|---|---|
| 3,948,273 A | 4/1976 | Sanders |
| 4,214,593 A | 7/1980 | Imbruce et al. |
| 4,305,392 A | 12/1981 | Chester |
| 4,344,436 A | 8/1982 | Kubota |
| 4,423,725 A | 1/1984 | Baran et al. |
| 4,488,548 A | 12/1984 | Agdanowski |
| 4,498,473 A | 2/1985 | Gereg |
| 4,502,482 A | 3/1985 | DeLuccia et al. |
| 4,762,125 A * | 8/1988 | Leiman et al. ........... 128/207.15 |
| 4,840,173 A | 6/1989 | Porter, III |
| 5,058,577 A | 10/1991 | Six |
| 5,067,497 A | 11/1991 | Greear |
| 5,431,637 A | 7/1995 | Okada |
| 5,445,144 A | 8/1995 | Wodicka et al. |
| 5,582,167 A | 12/1996 | Joseph |
| 5,676,635 A | 10/1997 | Levin |
| 5,819,723 A | 10/1998 | Joseph |
| 5,855,203 A * | 1/1999 | Matter ..................... 128/207.14 |
| 6,062,223 A | 5/2000 | Palazzo et al. |
| 6,796,309 B2 * | 9/2004 | Nash et al. ............... 128/207.14 |

(Continued)

OTHER PUBLICATIONS

Kolobow et al.; "The Mucus Slurper: a novel tracheal tube that requires no tracheal tube suctioning. A preliminary report.;" Intensive Care Med., 2006, vol. 32; pp. 1414-1418.

(Continued)

*Primary Examiner* — Bradley Philips
(74) *Attorney, Agent, or Firm* — Fletcher Yoder PC

(57) ABSTRACT

The present disclosure describes systems and methods that utilize a tracheal tube with a shaped evacuation port. An evacuation port coupled to a suction lumen may be shaped to reduce air channel formation within the suction lumen, which in turn may improve the suctioning force and efficiency. The shaped evacuation ports may be generally oval or may be shaped to minimize a height dimension while maintaining a suitable cross-sectional area. In particular embodiments, the shaped evacuation ports may have cross-sectional areas that correspond to a cross-sectional area of the suction lumen.

14 Claims, 7 Drawing Sheets

(56) References Cited

U.S. PATENT DOCUMENTS

| | | | |
|---|---|---|---|
| 6,849,042 B2 | 2/2005 | Christopher | |
| 7,052,456 B2 | 5/2006 | Simon | |
| 7,089,942 B1 | 8/2006 | Grey | |
| 7,152,603 B1 | 12/2006 | Crump et al. | |
| 7,156,827 B2 | 1/2007 | McNary et al. | |
| 7,191,782 B2 | 3/2007 | Madsen | |
| 7,273,050 B2 | 9/2007 | Wei | |
| 7,293,561 B2 | 11/2007 | Madsen et al. | |
| 2004/0194785 A1* | 10/2004 | Miller | 128/207.14 |
| 2005/0039754 A1 | 2/2005 | Simon | |
| 2007/0028924 A1 | 2/2007 | Madsen et al. | |
| 2007/0028925 A1 | 2/2007 | Madsen et al. | |
| 2007/0044806 A1* | 3/2007 | Madsen et al. | 128/207.15 |
| 2007/0044807 A1 | 3/2007 | Madsen et al. | |
| 2008/0011304 A1 | 1/2008 | Stewart | |
| 2008/0047562 A1 | 2/2008 | Colburn et al. | |
| 2008/0099025 A1 | 5/2008 | MacMillan et al. | |
| 2008/0110468 A1 | 5/2008 | Nelson et al. | |
| 2008/0210235 A1 | 9/2008 | Field et al. | |
| 2008/0257353 A1 | 10/2008 | Yamamoto et al. | |
| 2008/0283052 A1* | 11/2008 | Young | 128/200.26 |
| 2009/0038620 A1 | 2/2009 | Efrati | |
| 2009/0071484 A1 | 3/2009 | Black et al. | |
| 2009/0260625 A1* | 10/2009 | Wondka | 128/203.12 |
| 2010/0113916 A1* | 5/2010 | Kumar | 600/424 |
| 2010/0258134 A1 | 10/2010 | Colburn et al. | |
| 2011/0023884 A1* | 2/2011 | Cuevas et al. | 128/207.14 |
| 2011/0146691 A1 | 6/2011 | Burnett et al. | |

OTHER PUBLICATIONS

L. Lorente, et al.; "Influence of an Endotracheal Tube Polyurethane Cuff and Subglottic Secretion Drainage on Pneumonia;" American Journal of Respiratory and Critical Care Medicine, 2007, vol. 76, pp. 1079-1083.

P. O'Neal, et al.; "Sublottic Secretion Viscosity and Evacuation Efficiency," Biological Research for Nursing, vol. 8, No. 3, Jan. 2007, pp. 202-209; also found at http://brn.sagepub.com/cgi/content/abstract/8/3/202.

F. Bassi, et al.; "A 72-hour study to test the efficacy and safety of the "Mucus Slurper" in mechanically ventilated sleep;" Crit. Car. Med., 2007, vol. 35, No. 3, pp. 906-911.

Richard Branson, "Secretion Management in the Mechanically Ventilated Patient;" Respiratory Care, Oct. 2007, vol. 52, No. 10, pp. 1328-1347.

NCT00341354: Clinical Trials.Gov; "Coated Endotracheal Tube and Mucus Shaver to Prevent Hospital-Acquired Infections;" Jun. 19, 2006, 3pgs.

NCT00663637: Clinical Trials.Gov; "Removal of Endotracheal Tube Secretions Comprehensively Until Extubation (RESCUE);" Apr. 18, 2008, 3 pgs.

NCT00374959: Clinical Trials.Gov; "Prevention of Pneumonia Comparing Ceftriaxone with Subglottic Aspiration;" Sep. 11, 2006, 4 pgs.

NCT00450476: Clinical Trials.Gov; "Aspiration of Subglottic Secretions Using Hi-Lo Evac Endotracheal Tube: Tube Size and Incidence of Suction Lumen Dysfunction;" Mar. 21, 2007, 3 pgs.

Cook Medical Product Brochure / Critical Care / Endobronchial Blockers found at http://www.cookmedical.com/cc/familyListingAction.do?family=Endobronchial+Blockers ; 2pgs.

Hudson RCI Products Brochure / Airway Management: Endotracheal Tubes and Accessories, Teleflex ISIS HVT, found at http://www.hudsonrci.com/Products/product_results.asp?catalog=1∏_cat=21∏_subcat=38; 5 pgs.

Hudson RCI Products Brochure / Airway Management: Endotracheal Tubes and Accessories, Sherican Sher-I-Bronch, found at http://www.hudsonrci.com/Products/product_results.asp?catalog=1∏_cat=21∏_subcat=38; 4 pgs.

Teleflex Medical Product Brochure / Rusch / Airway Management: Endotracheal Tubes and Accessories, Rusch Easytube Double Lumen Tube, found at http://www.hudsonrci.com/Products/product_results.asp?catalog=1∏_cat=21∏_subcat=38; 7 pgs.

Smiths Airway Products Brochure / Portex / Endobrochial Tubes 24 pgs.

* cited by examiner

SHAPED EVACUATION PORT FOR A MULTI-LUMEN TRACHEAL TUBE

BACKGROUND

The present disclosure relates generally to medical devices and, more particularly, to tracheal tubes that include an evacuation lumen and an evacuation port that facilitates suctioning of patient secretions.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tracheal tube (e.g., endotracheal, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal. Such seals may be formed by inflation of a balloon cuff inside the trachea that contacts the tracheal walls.

The tracheal seal may also prevent or reduce ingress of solid or liquid matter into the lungs from proximal to the seal. In particular, normal swallowing and draining activities of the upper respiratory tract may be disrupted by intubation. Accordingly, secretions (e.g., mucus and saliva) formed in the mouth may gather and pool above a shelf formed by the inflated tracheal cuff. To reduce any migration of this material past the seal of the cuff and into the lungs, clinicians may manage the accumulation of secretions around the seal of the cuff via external suctioning. For example, some tracheal tubes include a dedicated lumen formed in the wall of the tracheal tube that includes a port or opening configured to access any pooled secretions. When negative pressure is applied to the lumen, for example via a syringe, the secretions enter the lumen through the port and are removed from the patient.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
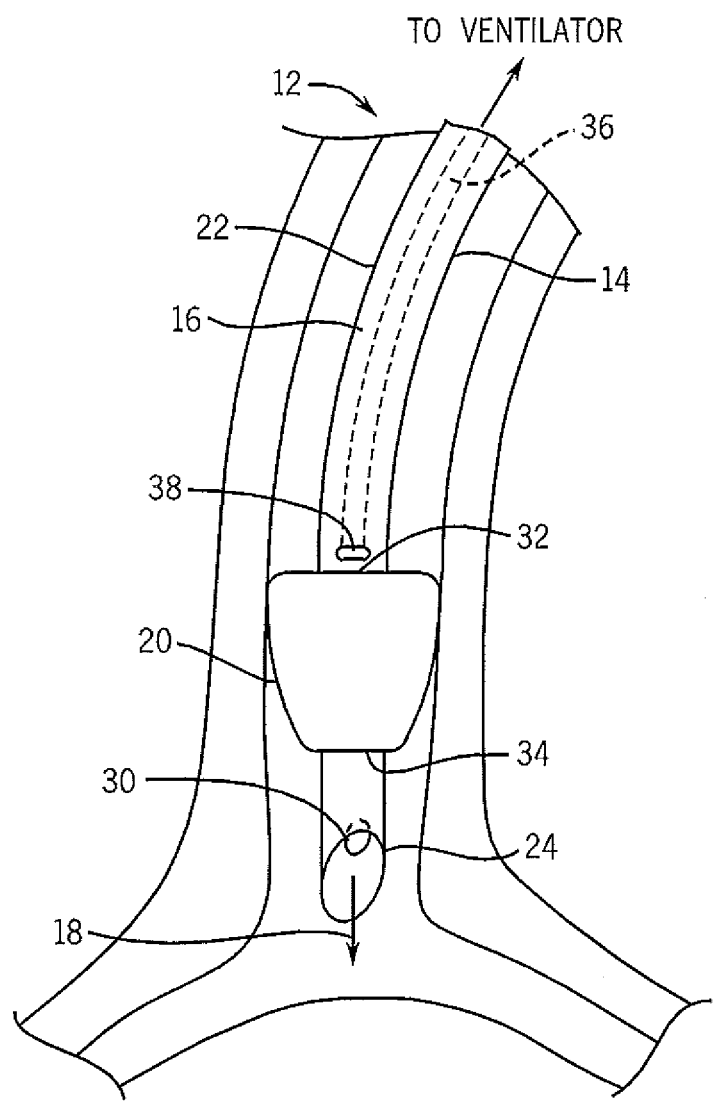
FIG. 1 is a side view of an inserted tracheal tube in accordance with embodiments of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Inserted airway devices, e.g., tracheal tubes, may interfere with the normal drainage systems of the mouth and throat. For devices that include inflatable balloon cuffs to seal the lower airway space, the balloon cuff forms a physical barrier to the drainage of liquid secretions that form in the mouth, which may accumulate on top of the cuff. The accumulated secretions may be suctioned away, for example via a dedicated suction lumen formed in a wall of the device. Typically, such suctioning is intermittent, and the pool of secretions is removed through an evacuation port located above the inflated balloon cuff. Over time, a volume of secretions may pool above the cuff such that the evacuation port is at least partly covered by the secretions. As secretions are removed via the evacuation port, the total volume of accumulated secretions is reduced, which exposes the evacuation port to more air than secretions. In such an environment, the evacuation port suctions in a mix of air and secretions, which reduces the efficiency of suctioning and increases the likelihood of air channel formation. In particular, the formation of an air channel in the suction lumen causes a nonlinear slowdown in suctioning efficiency.

As described in detail below, embodiments of tracheal tubes having shaped evacuation ports are provided herein. In particular, the disclosed tracheal tubes include one or more dedicated suction lumens that terminate in a shaped evacuation port. The evacuation ports as provided improve suctioning by reducing the incidence of air channel formation within suctioned material. For example, such evacuation ports may be generally shaped to minimize a height dimension, which may reduce or delay the exposure to air as the secretion levels drop during suctioning. Such evacuation ports may have elongated dimensions about the circumference of the tube, which allows the size of the evacuation port to remain large enough to pull viscous materials into the suction lumen. In one embodiment, the evacuation ports may be generally oval-shaped. In another embodiment, the dimensions of the evacuation port may be matched to the cross-sectional area of the suction lumen. That is, despite having different cross-sectional shapes, the cross-sectional areas of the evacuation port and the suction lumen may be about the same. Such an implementation may facilitate efficient movement of fluid through the evacuation port and into the suction lumen.

The tracheal tubes as provided herein are disposable rather than reusable, capable of providing differential mechanical ventilation to either or both lungs, and capable of supporting all other functions of standard endotracheal tubes (e.g. sealing, positive pressure generation, suctioning, irrigation, drug instillation, etc). The tracheal tubes can be used in conjunction with all acceptable auxiliary airway devices such as (e.g. heat and humidity conservers, mechanical ventilators, humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as endotracheal tubes, it should be noted that presently contemplated embodiments may include a shaped evacuation port used in conjunction with other types of airway devices. For example, the disclosed embodiments may be used in conjunction with a single-lumen tube, tracheostomy tube, a double-lumen tube (e.g., a Broncho-Cath™ tube), a specialty tube, or any other airway device with a main ventilation lumen. Indeed, any device with a suction lumen designed for use in an airway of a patient may include an evacuation port as provided. As used herein, the term "tracheal tube" may include an endotracheal tube, a tracheostomy tube, a double-lumen tube, a bronchoblocking tube, a specialty tube, or any other airway device.

Turning now to the drawings, FIG. 1 is a perspective view of an exemplary tracheal tube 12 with a shaped evacuation port and configured to be placed in a patient's airway in accordance with aspects of the present disclosure. The tracheal tube 12 includes a central tubular body 14 that defines a ventilation lumen 16 that facilitates the transfer of gases to and from the lungs, e.g., as airflow into the lungs shown by arrow 18. The tracheal tube 12 includes an inflatable cuff 20 disposed towards a distal end 24. The distal end 24 terminates in an opening 26. A proximal end of the tracheal tube 12 may connect to upstream airway devices (e.g., a ventilator). A Murphy eye 30 may be located on the tubular body 14 opposite the opening 26 to prevent airway occlusion when the tracheal tube 12 is improperly placed within the patient's trachea.

The cuff 20 is configured to seal the tracheal space once inflated against the tracheal walls. The cuff 20 is typically affixed to an exterior wall 22 of the tubular body 14 via a proximal shoulder 32 and a distal shoulder 34. As noted, the present disclosure relates to tracheal tubes with one or more shaped evacuation ports. For example, the tracheal tube 12 may include a suction lumen 36 that terminates in an evacuation port 38 located above the proximal shoulder 32.

Figure 2:
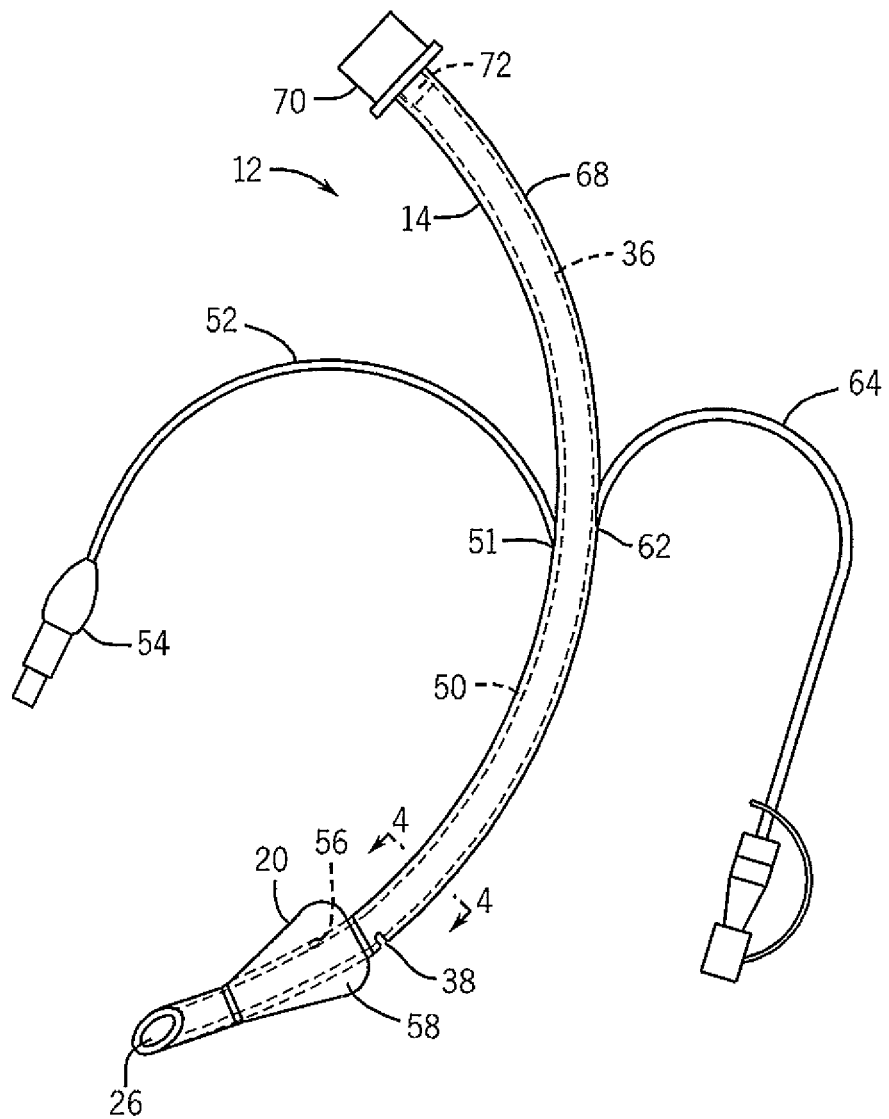
FIG. 2 is a perspective view of a tracheal tube with an evacuation port in accordance with embodiments of the present disclosure.

As shown in greater detail in perspective view in FIG. 2, the tracheal tube 12 may include separate dedicated lumens for cuff inflation and suction. For example, the cuff 20 may be inflated via inflation lumen 50 that emerges from the tubular body 14 at a junction 51 and terminates at its proximal end in an inflation tube 52 connected to an inflation pilot balloon and valve assembly 54. The inflation lumen 50 terminates in notch 56, which is in fluid communication with the interior space 58 of the cuff 20. Additionally, it should be noted that the cuff 20 may be any suitable cuff, such as a tapered cuff, a non-tapered cuff, and so forth. The tracheal tube 12 also includes a suction lumen 36 that extends along the tracheal tube 12 and emerges from a junction 62 on the tracheal tube 12 proximal of the vocal cords 40 (see FIG. 1) to a suction line 64. The suction lumen 36 is in fluid communication with the evacuation port 38 for suctioning secretions into the suction lumen 36, and out of the tube via the suction line 64.

The tracheal tube 12 and the cuff 20, as well as any associated lumens, are formed from materials having suitable mechanical properties (such as puncture resistance, pin hole resistance, tensile strength), chemical properties (such as biocompatibility). In one embodiment, the walls of the cuff 20 are made of a polyurethane having suitable mechanical and chemical properties. An example of a suitable polyurethane is Dow Pellethane® 2363-80A. In another embodiment, the walls of the cuff 20 are made of a suitable polyvinyl chloride (PVC). In certain embodiments, the cuff 20 may be generally sized and shaped as a high volume, low pressure cuff that may be designed to be inflated to pressures between about 15 cm $H_2O$ and 30 cm $H_2O$. However, it should be understood that the intracuff pressure may be dynamic. Accordingly, the initial inflation pressure of the cuff 20 may change over time or may change with changes in the seal quality or the position of the cuff 20 within the trachea. The tracheal tube 12 may be coupled to a respiratory circuit (not shown) that allows one-way flow of expired gases away from the patient and one-way flow of inspired gases towards the patient. The respiratory circuit, including the tracheal tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene. In addition, the tracheal tube may feature a Magill curve. In one embodiment, the suction lumen 36 and evacuation port 38 may be positioned on an outside surface 68 of the curve, such that the evacuation port 38 generally faces a dorsal side when inserted into the patient. The tracheal tube 12 may also include a connector 70 at its proximal end 72 for connection to upstream devices via appropriate tubing. The lumens (e.g., ventilation lumen 16, inflation lumen 50, and/or suction lumen 36) may be formed in the tubular body 14 via an extrusion process. In such an implementation, the lumens run alongside the airflow path of the ventilation lumen 16 from the proximal end 72 to the distal end 24.

The evacuation port 38 may be formed in the tubular body 14 by any suitable process, including milling, drilling, cutting, hotwire methods, laser milling or cutting, and water jet techniques. Further, in a specific embodiment, the evacuation port 38 may be formed on the tubular body 14 after the cuff 20 is applied such that the evacuation port 38 and the proximal shoulder 32 of the cuff 20 are appropriately aligned. However, in other embodiments, the evacuation port 38 may be formed at an earlier stage in the manufacturing process, and the cuff 20 may be applied after the evacuation port 38 has been formed. In addition, the evacuation port 38 may be formed relative to appropriate indicators or marks on the tubular body 14. In one embodiment, the tube 12 may include a marking that may be used to orient a laser or other cutting tool.

Figure 3:
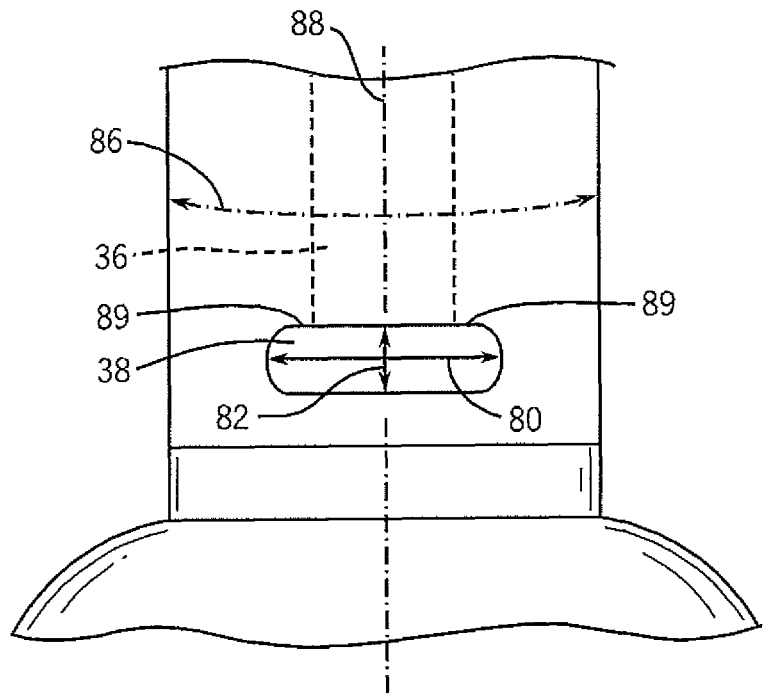
FIG. 3 is a detail view of the evacuation port of the tracheal tube of FIG. 2.

FIG. 3 is a detailed view of one implementation of an evacuation port 38 in which the evacuation port 38 is generally ovoid. In specific embodiments, the evacuation port may be an ellipse. The evacuation port includes a major diameter 80 and a minor diameter 82. In the depicted embodiment, the minor diameter 82 is generally along the flow path of the tracheal tube 12. The major diameter 80 form a part of the outer circumference 86 of the tubular body 14 and is approximately orthogonal to the minor diameter 82. However, it should be understood that, in particular implementations, in may be advantageous to change the orientation of the evacuation port 38. For example, the evacuation port 38 may be slightly tilted such that the major diameter 80 is offset from a plane orthogonal to the flow path (e.g., along axis 88) of the tracheal tube.

Further, while the evacuation port 38 is depicted as an oval, other shapes may achieve improved suctioning as provided herein. In certain embodiments, the evacuation port 38 may have a rectangular shape, a slit shape, or irregular shape that is generally elongated about the circumference 86 of the tubular body 14 relative to a dimension along the axis 88 of the flow path. In particular, in one embodiment, the evacuation port 38 is characterized by having a shortest dimension along the flow path 88 and a longest dimension that is along a portion of the circumference 86. In a particular embodiment, the shortest dimension or minor diameter 82 may be equal to or less than 4 mm, equal to or less than 3.5 mm, or equal to or less than 3 mm. As noted, the longest dimension or major diameter 80 may be elongated relative to the shortest dimension or minor diameter 82. For example, for a shortest dimension of less than 3 mm, the longest dimension may be at least 5 mm. Accordingly, the area of the evacuation port 38 that is exposed to air as the secretion levels drop during suctioning is reduced relative to a round shape. In certain embodiments, the longest dimension (e.g., the major diameter 80) is wider than the suction lumen 36. For example, for a suction lumen that is 3 mm in diameter, the evacuation port 38 may include portions 89 that extend about the circumference 86 beyond the lumen.

Figure 4:
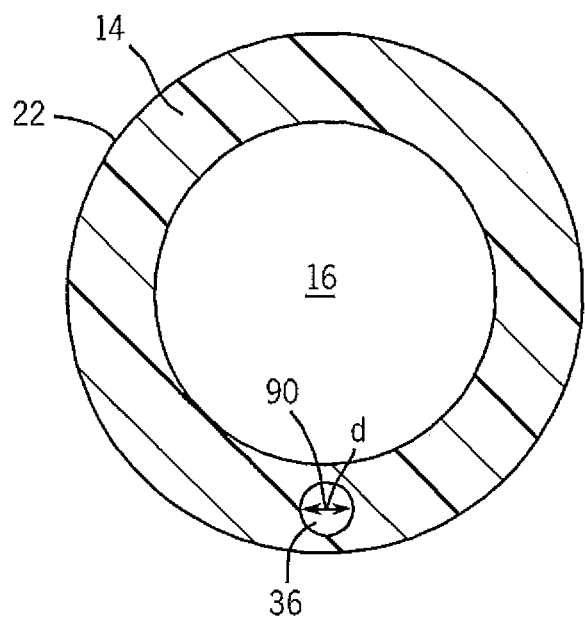
FIG. 4 is a cross-sectional view of the tracheal tube of FIG. 2.

In a specific implementation, the evacuation port 38 is formed such that its cross-sectional area is approximately equal to a cross-sectional area of the suction lumen 36. FIG. 4 is a cross-sectional view of the suction lumen 36, showing an internal diameter 90. The cross-section is taken along a plane approximately orthogonal to the flow path of the suction lumen 36 (or the tubular body 14). In certain embodiments, the internal diameter of the suction lumen 36 may be equal to or less than 5 mm or equal to or less than 3 mm. It should be understood that the diameter of the suction lumen 36 may be selected in conjunction with an appropriate tube size. That is, larger tracheal tubes 12 may include larger suction lumens 36 and smaller tubes 12 may includes suction lumens 36 with relatively smaller diameters. In one embodiment, the dimensions of the evacuation port 38 may be determined using the following equation:

$$A = \pi a_{major} b_{minor}$$

The area A is the same for the suction lumen 36 and the evacuation port 38, e.g., the cross-sectional area A of the evacuation port 38 may be determined by setting A to the cross-sectional area of the suction lumen 36. In turn, the cross-sectional area of the suction lumen 36 may be calculated by using the internal diameter of the suction lumen 36. The dimensions of the major diameter and minor diameter may be solved for a range of possible values. In particular embodiments, the range for the major diameter may be selected to maintain tube integrity. In one embodiment, the major diameter may be less than 50% of the circumference of the suction lumen 36.

Figure 5:
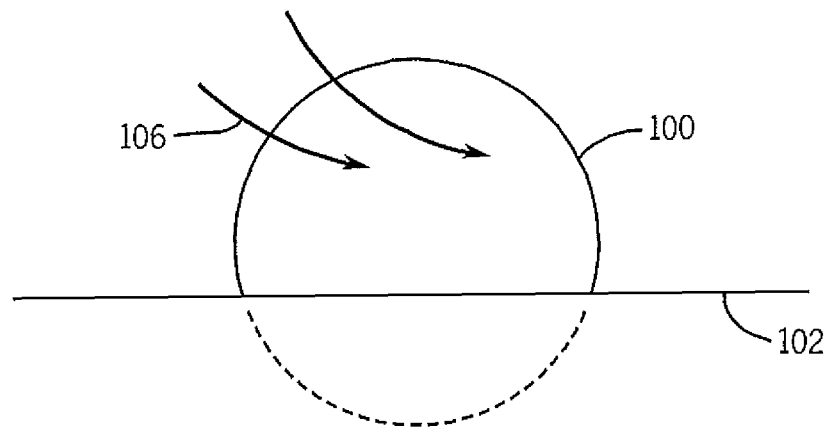
FIG. 5 is an illustration of air flow into a round evacuation port.
Figure 6:
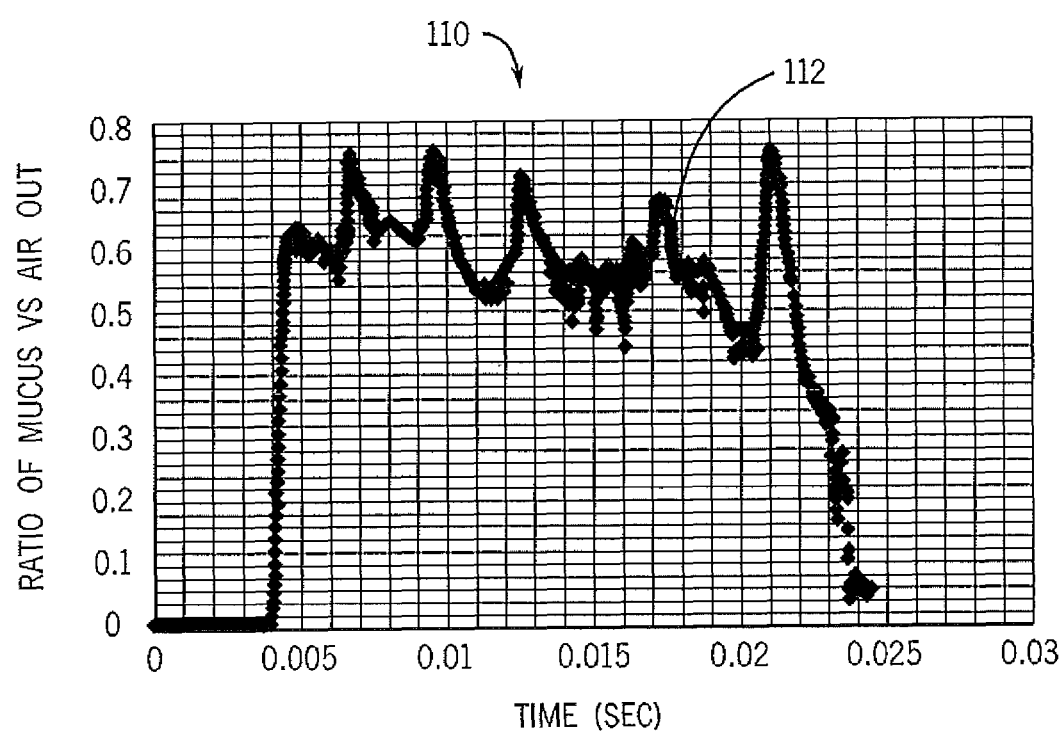
FIG. 6 is plot of a ratio of mucus evacuated with respect to time for a conventional round evacuation port.
Figure 7:
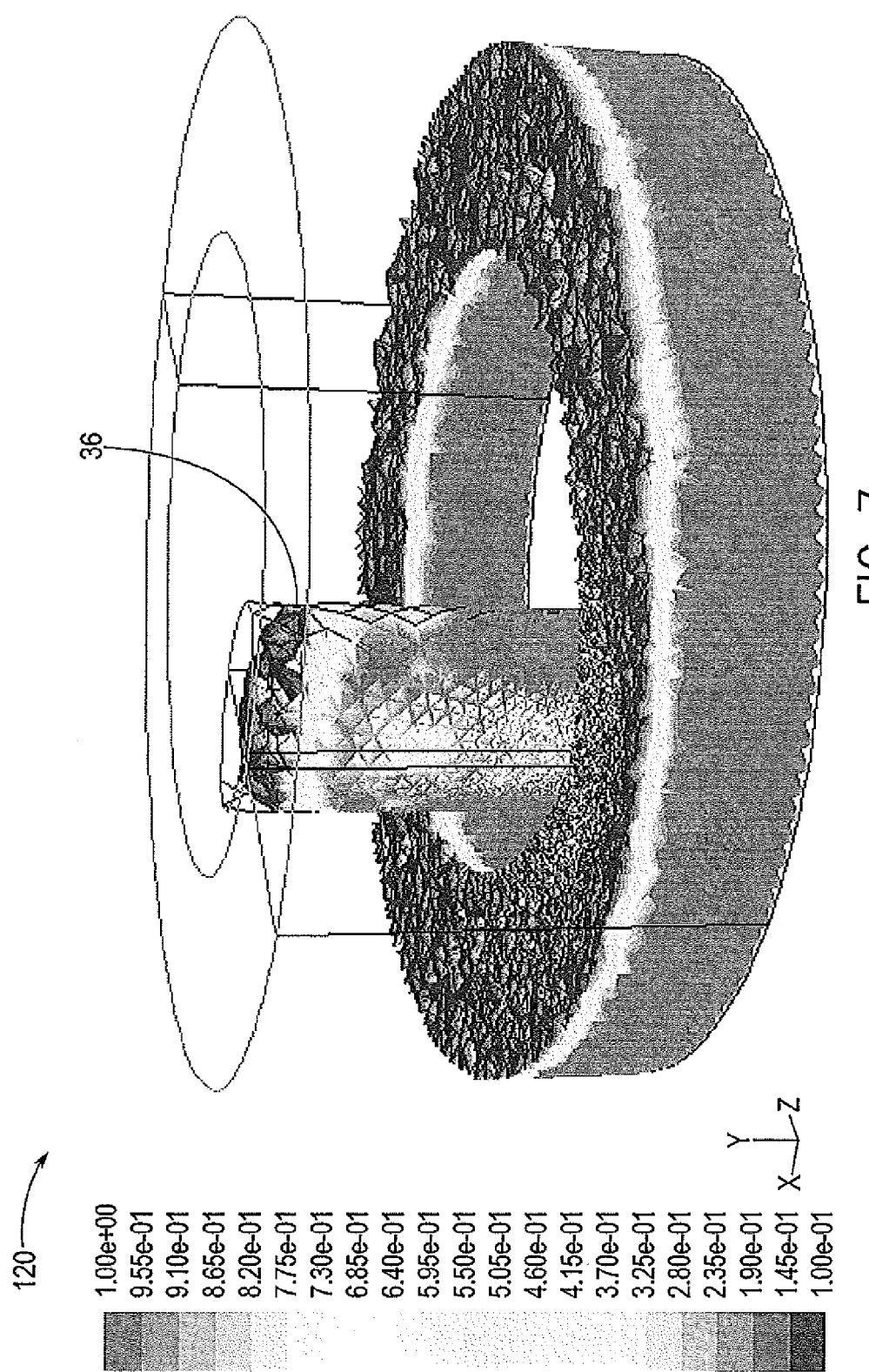
FIG. 7 is phase contour model of mucus suction in a conventional evacuation port.
Figure 8:
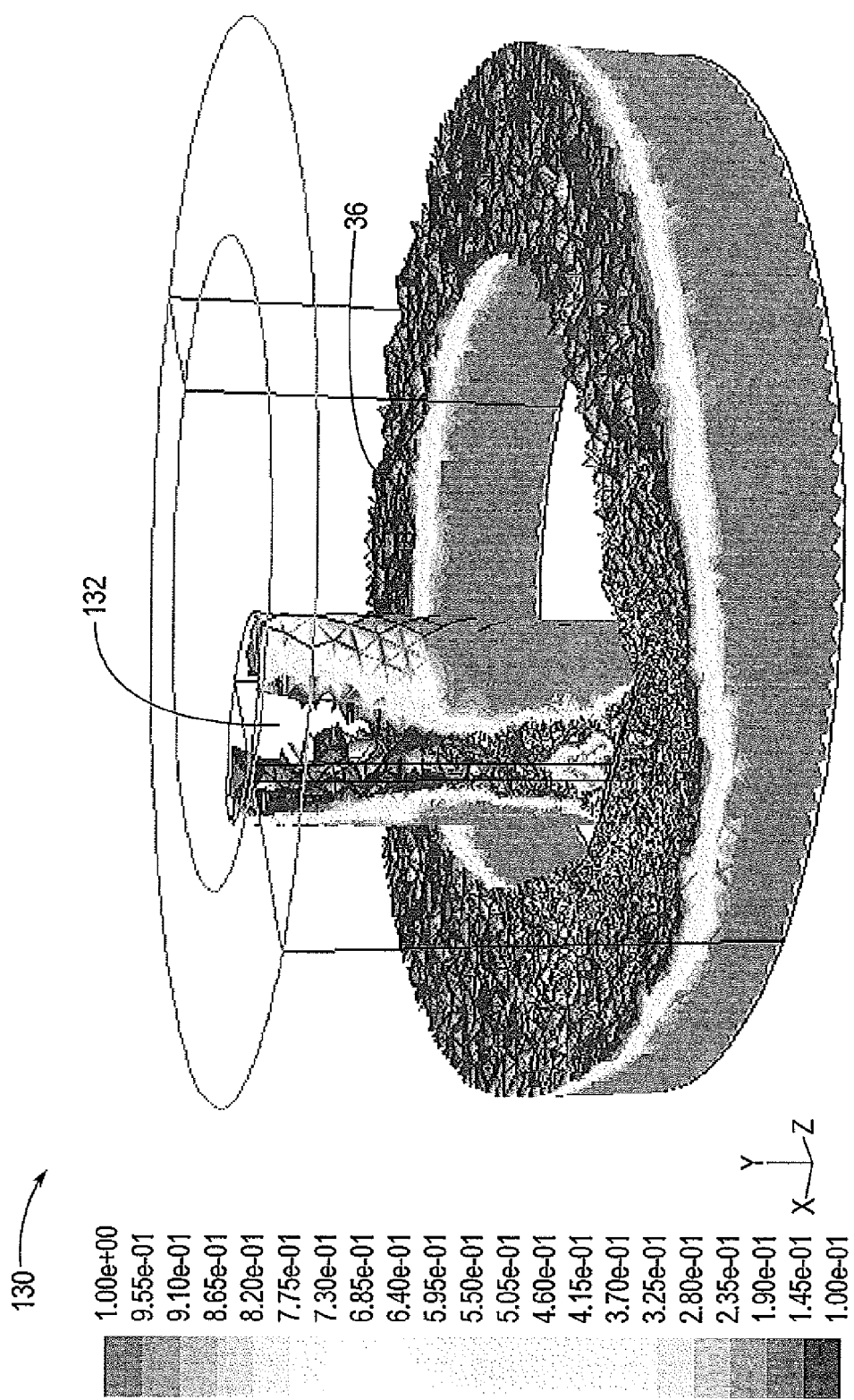
FIG. 8 is phase contour model of an air channel formed in a conventional evacuation port.

FIG. 5 is a schematic view of a round evacuation port 100 partially covered by secretions 102. As the secretion levels drop, air is suctioned into the evacuation port 100, which reduces the suctioning efficiency. In one example of the disclosed embodiments, a generally round evacuation port was tested for fluid evacuation in a glass trachea. Artificial mucus solution was added to the system and suctioned out. FIG. 6 is a plot 110 of the ratio of mucus to air over time. As shown, over time, the amount of mucus suctioned out, shown as line 112, falls off after 0.02 seconds. These results are confirmed by phase contour plots taken during the testing process. FIG. 7 is a phase contour plot 120 of the system taken at 0.0004 seconds showing flow through a suction lumen 36 for the round evacuation port. FIG. 8 is a phase contour plot 130 of air channel formation at 0.0024 seconds for the same system, when the amount of mucus evacuated is greatly reduced. An air channel 132 is visible in the suction lumen 36. The emergence of the air channel 132 corresponds with the slowdown of suction, as shown in FIG. 6. Air channel formation, as shown with a round evacuation port design, may result in a nonlinear slowdown or complete cessation in mucus suctioning. Accordingly, because the evacuation port 38 as provided herein may result in reduced air channel formation, the incidence of such slowdowns or stoppages may also be reduced.

Figure 9:
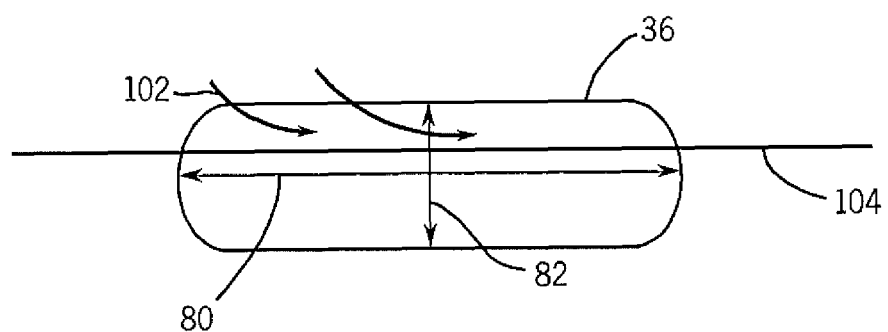
FIG. 9 is an illustration of reduced air flow into a shaped evacuation port in accordance with embodiments of the present disclosure.

FIG. 9 is a schematic diagram of an evacuation port 38 as provided with an elongated shape. The configuration of the elongated major diameter 80 and the reduced minor diameter 82 results in less surface area of the evacuation port 38 exposed to air for the a particular volume of fluid relative to a round design. For fluid flowing under Mach 1, as the cross sectional area increases, the effective suction pressure decreases. As provided herein, by decreasing the cross section of the evacuation port 38, the effective pressure can be increased. When the cross section of the evacuation port 38 opening is about equal to the cross section of the evacuation lumen 36, the effective suction pressure will be the same.

Table 1 shows the results of experiments performed with two different evacuation port sizes relative to a control round shape. Design #1 refers to an evacuation port with a shortest dimension or minor diameter of about 4 mm and design #2 refers to an evacuation port with a shortest dimension or minor diameter of about 3.5 mm. Relative to design #1, design #2 included a major diameter that was longer. Both design #1 and design #2 featured evacuation ports in which the major diameter was oriented about the circumference of the tube and the minor diameter was approximately orthogonal (e.g., was along the flow path of the tube) to the major diameter. These designs were compared to a round evacuation port with a diameter of 5.8 mm. Both design #1 and design #2 were elongated in the major diameter relative to the round port design.

TABLE 1

Results of suction testing for different evacuation port designs.

| | | Artificial mucus added to system | | | | | | |
|---|---|---|---|---|---|---|---|---|
| | | 0.285 mL | 0.307 mL | 0.679 mL | 0.75 mL | 1 mL | 2 mL | 5 mL |
| Round port | Mucus height after suction (mm) | No mucus evacuated | No mucus evacuated | No mucus evacuated | 3.1 | 3.1 | 3.1 | 3.1 |
| | Volume remaining (mL) | | | | 0.679 | 0.679 | 0.679 | 0.679 |
| | Volume evacuated (mL) | | | | 0.071 | 0.321 | 1.321 | 4.321 |
| Design #1 | Mucus height after suction (mm) | No mucus evacuated | No mucus evacuated | 1.4 | 1.4 | 1.4 | 1.4 | 1.4 |
| | Volume remaining (mL) | | | 0.307 | 0.307 | 0.307 | 0.307 | 0.307 |
| | Volume evacuated (mL) | | | 0.372 | 0.443 | 0.443 | 1.693 | 4.693 |
| Design #2 | Mucus height after suction (mm) | No mucus evacuated | 1.3 | 1.3 | 1.3 | 1.3 | 1.3 | 1.3 |
| | Volume remaining (mL) | | 0.285 | 0.285 | 0.285 | 0.285 | 0.285 | 0.285 |
| | Volume evacuated (mL) | | 0.022 | 0.394 | 0.465 | 0.715 | 1.715 | 4.715 |

TABLE 1-continued

Results of suction testing for different evacuation port designs.

| | | Artificial mucus added to system | | | | | | |
|---|---|---|---|---|---|---|---|---|
| | | 0.285 mL | 0.307 mL | 0.679 mL | 0.75 mL | 1 mL | 2 mL | 5 mL |
| Comparison | Design #1 over round port | | | | 627% | 216% | 128% | 109% |
| | Design #2 over round port | | | | 658% | 223% | 130% | 109% |
| | Design #2 over design #1 | | | | 105% | 103% | 101% | 100% |

In the testing system, different volumes of an artificial mucus solution were added and suctioned out. The suctioning efficiency was determined by the volume removed as well as the volume remaining and the height of the fluid remaining in the system. In the round port and for certain volumes tested with design #1 and design #2, low fluid volumes presented the greatest risk of air channel formation, because low volumes were more likely to only partially cover the evacuation ports tested. However, the reduced minor diameter dimensions for designs #1 and #2 showed improved suctioning at most fluid volumes relative to the round port. In particular, all of the designs did not suction the smallest tested volume of 0.285 mL. Both design #1 and design #2 had improved performance for other volumes of mucus. The results indicate that the tested designs have greater ability to maintain suction at lower fluid volumes. Design #2 was shortest in the dimension along the tube length. This design was able to perform in suctioning tests for volumes down to 0.307 mL. The round port and design #1 were not able to suction at this volume. The results show that design #1 and design #2 may improve suctioning efficiency several-fold relative to a round design.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A tracheal tube, comprising:
a conduit defining a passageway for delivering gas to a patient's lungs comprising a proximal end and a distal end;
an inflatable balloon cuff coupled to an exterior wall of the conduit;
a suction lumen formed between the exterior wall and an interior wall of the conduit and having a first cross-sectional geometry and a first cross-sectional area; and
an evacuation port of the suction lumen comprising an opening having an outer perimeter positioned in an outermost portion of the exterior wall of the conduit, wherein the outer perimeter defines both a second cross-sectional geometry and a second cross-sectional area of the opening, wherein the second cross-sectional geometry is different from the first cross-sectional geometry, and wherein the second cross-sectional area is equal to the first cross-sectional area of the suction lumen.

2. The tracheal tube of claim 1, wherein the evacuation port comprises an oval shape.

3. The tracheal tube of claim 1, wherein the evacuation port comprises a longest dimension along a circumference of the tracheal tube.

4. The tracheal tube of claim 1, wherein the second cross-sectional area of the opening is approximately 12 mm or less.

5. The tracheal tube of claim 1, wherein the suction lumen is positioned on the tracheal tube such that the evacuation port opens to a dorsal side of the patient when the tracheal tube is inserted.

6. The tracheal tube of claim 1, wherein the suction lumen has an internal diameter of approximately 5 mm or less.

7. The tracheal tube of claim 1, wherein a circular cross-section formed in the suction lumen is orthogonal to a flow path of the suction lumen.

8. The tracheal tube of claim 1, wherein the opening comprises an ellipse.

9. The tracheal tube of claim 1, wherein the suction lumen has an internal diameter of approximately 3 mm or less.

10. The tracheal tube of claim 1, wherein the opening comprises a minor diameter of approximately 3.5 mm or less.

11. The tracheal tube of claim 1, wherein the opening comprises a minor diameter of approximately 4 mm or less.

12. The tracheal tube of claim 1, wherein the tracheal tube comprises an endotracheal tube.

13. The tracheal tube of claim 1, wherein the tracheal tube comprises a tracheostomy tube.

14. The tracheal tube of claim 1, wherein the opening comprises a rectangle.

* * * * *